US006960442B2

(12) United States Patent
Eickmann et al.

(10) Patent No.: US 6,960,442 B2
(45) Date of Patent: Nov. 1, 2005

(54) IMMUNOREACTIVE REGIONS OF GLYCOPROTEIN GPII OF VARICELLA ZOSTER VIRUS (VZV)

(75) Inventors: Markus Eickmann, Marburg (DE); Dorothee Gicklhorn, Gladenbach (DE); Klaus Radsak, Marburg (DE); Hans-Peter Hauser, Elnhausen (DE); Bernhard Giesendorf, Michelbach (DE)

(73) Assignee: Dade Behring Marburg GmbH, Marburg (DE)

( * ) Notice: Subject to any disclaimer, the term of this patent is extended or adjusted under 35 U.S.C. 154(b) by 9 days.

(21) Appl. No.: 10/127,733

(22) Filed: Apr. 23, 2002

(65) Prior Publication Data

US 2002/0150889 A1 Oct. 17, 2002

Related U.S. Application Data

(62) Division of application No. 09/219,797, filed on Dec. 23, 1998, now Pat. No. 6,414,116.

(30) Foreign Application Priority Data

Dec. 23, 1997 (DE) .......................................... 197 57 769

(51) Int. Cl.$^7$ ................................................. G01N 33/53
(52) U.S. Cl. ............................ 435/7.1; 435/5; 530/300; 530/350
(58) Field of Search ...................... 435/5, 7.1; 530/300, 530/350, 389.1; 436/501

(56) References Cited

U.S. PATENT DOCUMENTS

| 3,717,772 A | | 2/1973 | Engman | |
|---|---|---|---|---|
| 6,414,116 B1 | * | 7/2002 | Eickmann et al. | .......... 530/350 |

FOREIGN PATENT DOCUMENTS

| EP | 0 210 931 | * | 2/1987 |
|---|---|---|---|
| EP | 0 210 931 | | 8/1987 |
| EP | 0 353 809 | | 2/1990 |
| EP | 0 405 867 | | 1/1991 |

OTHER PUBLICATIONS

Davison, A., et al., "The Complete DNA Sequence of Varicella–Zoster Virus", J. Gen. Virol., vol. 67, pp. 1759–1816 (1986).
Keller, P., et al., "Identification and Structure of the Gene Encoding gpII, A Major Glycoprotein of Varicella–Zoster Virus", Virology, vol. 152, pp. 181–191 (1986).
Massaer, M., et al., "induction of Neutralizing Antibodies by Varicella–Zoster Virus gp11 Glycoprotein Express from Recombinant Vaccinia Virus", J. Gen. Virol., vol. 74, pp. 491–494 (1993).
Wasmuth, E., et al., "Sensitive Enzyme–Linked Immunosorbent Assay for Antibody to Varicella–Zoster Virus Using Purified VZV Glycoprotein Antigen", Journal of Medicinal Virology, vol. 32, pp. 189–1993 (1990).
A. Kjartansdottir A., et al., "B–cell Epitopes of Varicella–Zoster Virus Glycoprotein II", *Archives of Virology*, Jul. 1996, pp. 2465–2469.
C.M. Koropchak et al., "Investigation of Varicella–Zoster Infection by Polymerase Chain Reaction in the Immunocompetent Host with Actue Varicella", *Journal of Infectious Diseases*, May 1991, pp. 1016–1022.
Database WPI, Section CH, Week 199511, XP002143444 (JP 07–000199A), Jan. 1, 1995.
Hayward, "T–Cell Responses to Predicted Amphipathic Peptides of Varicella–Zoster Virus Glycoproteins II and IV", *Journal of Virology*, Bd. 64, NR 2 (XP000917048) 1999, pp. 651–655.

* cited by examiner

Primary Examiner—James Housel
Assistant Examiner—Myron G. Hill
(74) Attorney, Agent, or Firm—Heller Ehrman LLP

(57) ABSTRACT

The present invention relates to immunoreactive peptides that are homologous with the region encompassing amino acid positions 450 to 655 of glycoprotein II of varicella zoster virus. In this context, preference is given to those peptides corresponding to segments of amino acids 505 to 647, 517 to 597, 535 to 584 or 545 to 582. The immunoreactive peptides are useful for methods of diagnosing varicella zoster virus infection.

5 Claims, 14 Drawing Sheets

Figure 1

| | | | | | | | | | | | | |
|---|---|---|---|---|---|---|---|---|---|---|---|---|
| Glu | Phe | Ala | Met | Leu | Gln | Phe | Thr | Tyr | Asp | His | Ile | Gln | Glu | His | Val |
| Asn | Glu | Met | Leu | Ala | Arg | Ile | Ser | Ser | Ser | Trp | Cys | Gln | Leu | Gln | Asn |
| Arg | Glu | Arg | Ala | Leu | Trp | Ser | Gly | Leu | Phe | Pro | Ile | Asn | Pro | Ser | Ala |
| Leu | Ala | Ser | Thr | Ile | Leu | Asp | Gln | Arg | Val | Lys | Ala | Arg | Ile | Leu | Gly |
| Asp | Val | Ile | *Phe* | Val | Ser | Asn | Cys | Pro | Glu | Leu | Gly | Ser | Asp | Thr | Arg |
| Ile | Ile | Leu | Gln | Asn | Ser | Met | Arg | Val | Ser | Gly | Ser | Thr | Thr | Arg | Cys |
| Tyr | Ser | Arg | Pro | Leu | Ile | Ser | Ile | Val | Ser | Leu | Asn | Gly | Ser | Gly | Thr |
| Val | Glu | Gly | Gln | Leu | Gly | Thr | Asp | Asn | Glu | Leu | Ile | Met | Ser | Arg | Asp |
| Leu | Leu | Glu | Pro | Cys | Val | Ala | Asn | His | Lys | Arg | Tyr | Phe | Leu | Phe | Gly |
| His | His | Tyr | Val | Tyr | Tyr | Glu | Asp | Tyr | Arg | Tyr | Val | Arg | Glu | Ile | Ala |
| Val | His | Asp | Val | Gly | Met | Ile | Ser | Thr | Tyr | Val | Asp | Leu | Asn | Leu | Thr |
| Leu | Leu | Lys | Asp | Arg | Glu | Phe | Met | Pro | Leu | Gln | Val | Tyr | Thr | Arg | Asp |
| Glu | Leu | Arg | Asp | Thr | Gly | Leu | Leu | Asp | Tyr | Ser | Glu | Ile | Gln | | |

Figure 2A

```
      GAATTTGCTATGCTCCAGTTTACATATGACCACATTCAAGAGCATGTTAATGAAATGTTG
1348  --+---------+---------+---------+---------+---------+-------  1407
      CTTAAACGATACGAGGTCAAATGTATACTGGTGTAAGTTCTCGTACAATTACTTTACAAC
      GluPheAlaMetLeuGlnPheThrTyrAspHisIleGlnGluHisValAsnGluMetLeu
      E  F  A  M  L  Q  F  T  Y  D  H  I  Q  E  H  V  N  E  M  L
```

```
      GCACGTATCTCCTCGTCGTGGTGCCAGCTACAAAATCGCGAACGCGCCCTTTGGAGCGGA
1408  --+---------+---------+---------+---------+---------+-------  1467
      CGTGCATAGAGGAGCAGCACCACGGTCGATGTTTTAGCGCTTGCGCGGGAAACCTCGCCT
      AlaArgIleSerSerSerTrpCysGlnLeuGlnAsnArgGluArgAlaLeuTrpSerGly
      A  R  I  S  S  S  W  C  Q  L  Q  N  R  E  R  A  L  W  S  G
```

```
      CTATTTCCAATTAACCCAAGTGCTTTAGCGAGCACCATTTTGGATCAACGTGTTAAAGCT
1468  --+---------+---------+---------+---------+---------+-------  1527
      GATAAAGGTTAATTGGGTTCACGAAATCGCTCGTGGTAAAACCTAGTTGCACAATTTCGA
      LeuPheProIleAsnProSerAlaLeuAlaSerThrIleLeuAspGlnArgValLysAla
      L  F  P  I  N  P  S  A  L  A  S  T  I  L  D  Q  R  V  K  A
```

```
      CGTATTCTCGGCGACGTTATCTCCGTTTCTAATTGTCCAGAACTGGGATCAGATACACGC
1528  --+---------+---------+---------+---------+---------+-------  1587
      GCATAAGAGCCGCTGCAATAGAGGCAAAGATTAACAGGTCTTGACCCTAGTCTATGTGCG
      ArgIleLeuGlyAspValIleSerValSerAsnCysProGluLeuGlySerAspThrArg
      R  I  L  G  D  V  I  S  V  S  N  C  P  E  L  G  S  D  T  R
```

```
      ATTATACTTCAAAACTCTATGAGGGTATCTGGTAGTACTACGCGTTGTTATAGCCGTCCT
1588  --+---------+---------+---------+---------+---------+-------  1647
      TAATATGAAGTTTTGAGATACTCCCATAGACCATCATGATGCGCAACAATATCGGCAGGA
      IleIleLeuGlnAsnSerMetArgValSerGlySerThrThrArgCysTyrSerArgPro
      I  I  L  Q  N  S  M  R  V  S  G  S  T  T  R  C  Y  S  R  P
```

```
      TTAATTTCAATAGTTAGTTTAAATGGGTCCGGGACGGTGGAGGGCCAGCTTGGAACAGAT
1648  --+---------+---------+---------+---------+---------+-------  1707
      AATTAAAGTTATCAATCAAATTTACCCAGGCCCTGCCACCTCCCGGTCGAACCTTGTCTA
      LeuIleSerIleValSerLeuAsnGlySerGlyThrValGluGlyGlnLeuGlyThrAsp
      L  I  S  I  V  S  L  N  G  S  G  T  V  E  G  Q  L  G  T  D
```

```
      AACGAGTTAATTATGTCCAGAGATCTGTTAGAACCATGCGTGGCTAATCACAAGCGATAT
1708  --+---------+---------+---------+---------+---------+-------  1767
      TTGCTCAATTAATACAGGTCTCTAGACAATCTTGGTACGCACCGATTAGTGTTCGCTATA
      AsnGluLeuIleMetSerArgAspLeuLeuGluProCysValAlaAsnHisLysArgTyr
      N  E  L  I  M  S  R  D  L  L  E  P  C  V  A  N  H  K  R  Y
```

```
      TTTCTATTTGGGCATCACTACGTATATTATGAGGATTATCGTTACGTCCGTGAAATCGCA
1768  --+---------+---------+---------+---------+---------+-------  1827
      AAAGATAAACCCGTAGTGATGCATATAATACTCCTAATAGCAATGCAGGCACTTTAGCGT
      PheLeuPheGlyHisHisTyrValTyrTyrGluAspTyrArgTyrValArgGluIleAla
      F  L  F  G  H  H  Y  V  Y  Y  E  D  Y  R  Y  V  R  E  I  A
```

```
      GTCCATGATGTGGGAATGATTAGCACTTACGTAGATTTAAACTTAACACTTCTTAAAGAT
1828  --+---------+---------+---------+---------+---------+-------  1887
      CAGGTACTACACCCTTACTAATCGTGAATGCATCTAAATTTGAATTGTGAAGAATTTCTA
      ValHisAspValGlyMetIleSerThrTyrValAspLeuAsnLeuThrLeuLeuLysAsp
      V  H  D  V  G  M  I  S  T  Y  V  D  L  N  L  T  L  L  K  D
```

Figure 2B

```
      AGAGAGTTTATGCCGCTGCAAGTATATACAAGAGACGAGCTGCGGGATACAGGATTACTA
1888  --+---------+---------+---------+---------+---------+------  1947
      TCTCTCAAATACGGCGACGTTCATATATGTTCTCTGCTCGACGCCCTATGTCCTAATGAT
      ArgGluPheMetProLeuGlnValTyrThrArgAspGluLeuArgAspThrGlyLeuLeu
      R   E   F   M   P   L   Q   V   Y   T   R   D   E   L   R   D   T   G   L   L

GACTACAGTGAAATTCAA
1948  --+-----------+----  1965
      CTGATGTCACTTTAAGTT
      AspTyrSerGluIleGln
        D   Y   S   E   I   Q
```

Figure 3A

| No. | Status | IgG ELISA Reference Conj. 1:50 Serum 1:231 | IgG ELISA pQE gpII 4 µg/ml Conj. 1:50 Serum 1:100 | No. | Status | IgG ELISA Reference Conj. 1:50 Serum 1:231 | IgG ELISA pQE gpII 4 µg/ml Conj. 1:50 Serum 1:100 |
|---|---|---|---|---|---|---|---|
| 1 | + | 1014 | 963 | 35 | + | 169 | 150 |
| 2 | + | 302 | 174 | 36 | + | 1613 | 1187 |
| 3 | + | 642 | 746 | 37 | - | 3 | 30 |
| 4 | + | 612 | 674 | 38 | - | 20 | 35 |
| 5 | + | 1383 | 419 | 39 | - | 2 | 56 |
| 6 | + | 930 | 1722 | 40 | - | 0 | 56 |
| 7 | + | 653 | 729 | 41 | + | 1254 | 1919 |
| 8 | + | 915 | 1086 | 42 | - | 25 | 50 |
| 9 | + | 570 | 607 | 43 | - | 15 | 43 |
| 10 | + | 1770 | >2500 | 44 | - | 58 | 38 |
| 11 | + | 990 | 222 | 45 | - | 13 | 32 |
| 12 | + | 698 | 427 | 46 | - | 64 | 61 |
| 13 | + | 141 | 249 | 47 | - | 68 | 49 |
| 14 | + | 338 | 590 | 48 | + | 1315 | 751 |
| 15 | + | 556 | 1074 | 49 | + | 1629 | 1423 |
| 16 | + | 791 | 615 | 50 | + | 469 | 142 |
| 17 | + | 2982 | >2500 | 51 | + | 693 | 813 |
| 18 | + | 1205 | 1736 | 52 | + | 1449 | 724 |
| 19 | + | 694 | 1157 | 53 | + | 1139 | 1170 |
| 20 | + | 1143 | 1134 | 54 | + | 1509 | 537 |
| 21 | + | 1405 | 1509 | 55 | + | 457 | 144 |
| 22 | + | 539 | 1091 | 56 | + | 343 | 102 |
| 23 | + | 2449 | >2500 | 57 | + | 1455 | 1233 |
| 24 | + | 1923 | 1605 | 58 | + | 1030 | 94 |
| 25 | + | 1420 | 654 | 59 | + | 528 | 122 |

Figure 3B

| 26 | Primary + | 1194 | 193 | 60 | + | 510 | 122 |
|----|-----------|------|-----|----|----|------|------|
| 27 | Zoster + | 2087 | 1719 | 61 | + | 300 | 113 |
| 28 | + | 549 | 714 | 62 | + | 490 | 152 |
| 29 | - | 34 | 207 | 63 | + | 888 | 308 |
| 30 | - | 76 | 88 | 64 | + | 1301 | 1087 |
| 31 | - | 0 | 53 | 65 | + | 704 | 549 |
| 32 | - | 41 | 89 | 66 | + | 2523 | 802 |
| 33 | - | 8 | 157 | 67 | + | 447 | 139 |
| 34 | - | 59 | 334 | 68 | + | 848 | 215 |

Figure 4A

| No. | Status | IgM ELISA Reference Conj. 1:50 Serum 1:42 | IgM ELISA pQE gpII 4 µg/ml Conj. 1:25 Serum 1:100 | No. | Status | IgM ELISA Reference Conj. 1:50 Serum 1:42 | IgM ELISA pQE gpII 4 µg/ml Conj. 1:25 Serum 1:100 |
|---|---|---|---|---|---|---|---|
| 1 | - | 11 | 41 | 29 | - | 16 | 55 |
| 2 | - | 22 | 54 | 30 | - | 8 | 44 |
| 3 | - | 16 | 77 | 31 | - | 3 | 48 |
| 4 | - | 57 | 80 | 32 | - | 50 | 48 |
| 5 | + | 133 | 70 | 33 | - | 9 | 72 |
| 6 | - | 0 | 38 | 34 | + | 250 | 131 |
| 7 | - | 10 | 55 | 35 | + | 291 | 68 |
| 8 | - | 47 | 51 | 36 | - | 26 | 40 |
| 9 | - | 7 | 51 | 37 | + | 139 | 63 |
| 10 | + | 132 | 63 | 38 | - | 38 | 35 |
| 11 | - | 71 | 66 | 39 | - | 26 | 49 |
| 12 | - | 0 | 57 | 40 | - | 49 | 55 |
| 13 | - | 17 | 39 | 41 | - | 5 | 37 |
| 14 | - | 11 | 53 | 42 | - | 27 | 96 |
| 15 | - | 23 | 45 | 43 | - | 51 | 40 |
| 16 | - | 11 | 52 | 44 | - | 8 | 43 |
| 17 | + | 979 | 270 | 45 | - | 21 | 39 |
| 18 | - | 9 | 42 | 46 | - | 10 | 49 |
| 19 | - | 34 | 73 | 47 | - | 29 | 38 |
| 20 | + | 293 | 232 | 48 | - | 30 | 67 |
| 21 | + | 126 | 117 | 49 | - | 21 | 34 |
| 22 | - | 61 | 86 | 50 | - | 56 | 82 |
| 23 | + | 292 | 49 | 51 | - | 5 | 56 |
| 24 | + | 581 | 54 | 52 | - | 97 | 24 |
| 25 | + | 321 | 77 | 53 | - | 2 | 28 |

Figure 4B

| 26 | + | 509 | 155 | 54 | 31 | 43 |
|----|---|-----|-----|----|----|----|
| 27 | + | 298 | 80  |    |    |    |
| 28 | - | 29  | 72  |    |    |    |

Figure 5

(1) GENERAL INFORMATION:

(i) APPLICANT:
(A) NAME: Dade Behring Marburg GmbH
(B) STREET: Emil-von-Behring-Str. 76
(C) CITY: Marburg
(E) COUNTRY: Deutschland
(F) POSTAL CODE (ZIP): 35001
(G) TELEPHONE: 06421/39-2332
(H) TELEFAX: 06421/39-3631

(ii) TITLE OF INVENTION: Immunreaktive Bereiche des Glycoproteins gpII des Varicella-Zoster-Virus (VZV)

(iii) NUMBER OF SEQUENCES 10

(iv) COMPUTER READABLE FORM:
(A) MEDIUM TYPE: Floppy disk
(B) COMPUTER: IBM PC compatible
(C) OPERATING SYSTEM: PC-DOS/MS-DOS
(D) SOFTWARE: PatentIn Release #1.0, Version #1.30 (EPO)

(v) CURRENT APPLICATION DATA:
APPLICATION NUMBER DE 197 57 767.9

(2) INFORMATION FOR SEQ ID NO. 1:

(i) SEQUENCE CHARACTERISTICS:
(A) LENGTH: 206 amino acids
(B) TYPE: amino acid
(C) STRANDEDNESS:
(D) TOPOLOGY: linear (ii) MOLECULE TYPE: protein (iii) HYPOTHETICAL: YES (vi) ORIGINAL SOURCE:
(A) ORGANISM: Varizella Zoster Virus
(B) STRAIN: Ellen (viii) POSITION IN GENOME:
(B) MAP POSITION: ORF31

(xi) SEQUENCE DESCRIPTION: SEQ ID NO: 1:

Glu Phe Ala Met Leu Gln Phe Thr Tyr Asp His Ile Gln Glu His Val
 1               5                  10                  15

Asn Glu Met Leu Ala Arg Ile Ser Ser Ser Trp Cys Gln Leu Gln Asn
        20               25              30

Arg Glu Arg Ala Leu Trp Ser Gly Leu Phe Pro Ile Asn Pro Ser Ala
  35             40              45

Leu Ala Ser Thr Ile Leu Asp Gln Arg Val Lys Ala Arg Ile Leu Gly
  50             55              60

Asp Val Ile Ser Val Ser Asn Cys Pro Glu Leu Gly Ser Asp Thr Arg
  65             70              75              80

Ile Ile Leu Gln Asn Ser Met Arg Val Ser Gly Ser Thr Thr Arg Cys
        85               90              95

Tyr Ser Arg Pro Leu Ile Ser Ile Val Ser Leu Asn Gly Ser Gly Thr
      100           105            110

Val Glu Gly Gln Leu Gly Thr Asp Asn Glu Leu Ile Met Ser Arg Asp
 115            120            125

Leu Leu Glu Pro Cys Val Ala Asn His Lys Arg Tyr Phe Leu Phe Gly
 130            135            140

His His Tyr Val Tyr Tyr Glu Asp Tyr Arg Tyr Val Arg Glu Ile Ala
 145            150            155           160

Val His Asp Val Gly Met Ile Ser Thr Tyr Val Asp Leu Asn Leu Thr
      165           170            175

Leu Leu Lys Asp Arg Glu Phe Met Pro Leu Gln Val Tyr Thr Arg Asp
 180            185            190

Glu Leu Arg Asp Thr Gly Leu Leu Asp Tyr Ser Glu Ile Gln
 195           200            205

(2) INFORMATION FOR SEQ ID NO: 2:

(i) SEQUENCE CHARACTERISTICS:
      (A) LENGTH: 618 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (vi) ORIGINAL SOURCE:
      (A) ORGANISM: Varizella Zoster Virus
      (B) STRAIN: ellen (viii) POSITION IN GENOME:

(B) MAP POSITION: ORF31

(xi) SEQUENCE DESCRIPTION SEQ ID NO. 2:

GAATTTGCTA TGCTCCAGTT TACATATGAC CACATTCAAG AGCATGTTAA
TGAAATGTTG    60

GCACGTATCT CCTCGTCGTG GTGCCAGCTA CAAAATCGCG AACGCGCCCT
TTGGAGCGGA    120

CTATTTCCAA TTAACCCAAG TGCTTTAGCG AGCACCATTT TGGATCAACG
TGTTAAAGCT    180

CGTATTCTCG GCGACGTTAT CTTCGTTTCT AATTGTCCAG AACTGGGATC
AGATACACGC    240

ATTATACTTC AAAACTCTAT GAGGGTATCT GGTAGTACTA CGCGTTGTTA
TAGCCGTCCT    300

TTAATTTCAA TAGTTAGTTT AAATGGGTCC GGGACGGTGG AGGGCCAGCT
TGGAACAGAT    360

AACGAGTTAA TTATGTCCAG AGATCTGTTA GAACCATGCG TGGCTAATCA
CAAGCGATAT    420

TTTCTATTTG GGCATCACTA CGTATATTAT GAGGATTATC GTTACGTCCG
TGAAATCGCA    480

GTCCATGATG TGGGAATGAT TAGCACTTAC GTAGATTTAA ACTTAACACT
TCTTAAAGAT    540

AGAGAGTTTA TGCCGCTGCA AGTATATACA AGAGACGAGC TGCGGGATAC
AGGATTACTA    600

GACTACAGTG AAATTCAA                                        618

(2) INFORMATION FOR SEQ ID NO: 3

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetische DNA"

(iii) HYPOTHETICAL: NO (vi) ORIGINAL SOURCE:
        (A) ORGANISM Varizella Zoster Virus
        (B) STRAIN Ellen (viii) POSITION IN GENOME:
   (B) MAP POSITION: ORF31

(xi) SEQUENCE DESCRIPTION: SEQ ID NO: 3:

GGAATTCCTT CTATGTTTGT TACGGCGGTT G (2) INFORMATION FOR SEQ ID NO: 4:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetische DNA"

(iii) HYPOTHETICAL: NO (vi) ORIGINAL SOURCE:
      (A) ORGANISM: Varizella Zoster virus (viii) POSITION IN GENOME:
      (B) MAP POSITION: ORF31

(xi) SEQUENCE DESCRIPTION: SEQ ID NO: 4:

GCTCTAGAGC ATTTACACCC CCGTTACATT CTCG (2) INFORMATION FOR SEQ ID NO: 5:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetische DNA"

(iii) HYPOTHETICAL: NO (vi) ORIGINAL SOURCE:
      (A) ORGANISM: Varizella Zoster Virus (viii) POSITION IN GENOME:
      (B) MAP POSITION: ORF31

(xi) SEQUENCE DESCRIPTION: SEQ ID NO: 5:

CGGGATCCCG TGTTAAAGCT CGTATTCTCG GCGACG (2) INFORMATION FOR SEQ ID NO: 6:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetische DNA"

(iii) HYPOTHETICAL: NO (vi) ORIGINAL SOURCE:
    (A) ORGANISM: Varizella Zoster Virus
    (B) STRAIN: Ellen (viii) POSITION IN GENOME:
    (B) MAP POSITION: ORF31

(xi) SEQUENCE DESCRIPTION: SEQ ID NO: 6:

CCCAAGCTTT AATCCTGTAT CCCGCAGCTC GTCTCT (2) INFORMATION FOR SEQ ID NO: 7:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetische DNA"

(iii) HYPOTHETICAL: NO (vi) ORIGINAL SOURCE:
    (A) ORGANISM: Varizella Zoster Virus
    (B) STRAIN: Ellen (viii) POSITION IN GENOME:
    (B) MAP POSITION: ORF31

(xi) SEQUENCE DESCRIPTION: SEQ ID NO: 7:

CGGGATCCGT TTCTAATTGT CCAGAACTGG GATCAG (2) INFORMATION FOR SEQ ID NO: 8:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetische DNA"

(iii) HYPOTHETICAL: NO (vi) ORIGINAL SOURCE:
      (A) ORGANISM: Varizella Zoster Virus
      (B) STRAIN: Ellen (viii) POSITION IN GENOME:
      (B) MAP POSITION: ORF31

(xi) SEQUENCE DESCRIPTION: SEQ ID NO: 8:

CCCAAGCTTA TACGTAGTGA TGCCCAAATA GAAAA (2) INFORMATION FOR SEQ ID NO: 9:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetische DNA"

(iii) HYPOTHETICAL: NO (vi) ORIGINAL SOURCE:
      (A) ORGANISM: Varizella Zoster virus
      (B) STRAIN: Ellen (viii) POSITION IN GENOME:
      (B) MAP POSITION: Orf31

(xi) SEQUENCE DESCRIPTION SEQ ID NO: 9:

CGGGATCCTC TATGAGGGTA TCTGGTAGTA CTACGCGTT (2) INFORMATION FOR SEQ ID NO: 10.

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetische DNA"

(iii) HYPOTHETICAL: NO (vi) ORIGINAL SOURCE:
        (A) ORGANISM: varizella Zoster Virus
        (B) STRAIN: Ellen (viii) POSITION IN GENOME:
        (B) MAP POSITION: ORF31

(xi) SEQUENCE DESCRIPTION: SEQ ID NO. 10:

CCCAAGCTTA GCCACGCATG GTTCTAACAG ATC

IMMUNOREACTIVE REGIONS OF GLYCOPROTEIN GPII OF VARICELLA ZOSTER VIRUS (VZV)

This application is a divisional of application Ser. No. 09/219,797 filed Dec. 23, 1998, which is now U.S. Pat. No. 6,414,116.

FIELD OF THE INVENTION

The present invention relates to immunoreactive peptides that are homologous with the region encompassing amino acid positions 450 to 655 of glycoprotein II of varicella zoster virus. More particularly, the invention relates to peptides that correspond to amino acids 505 to 647, 517 to 597, 535 to 584 or 545 to 582 of the protein. The immunoreactive peptides can be used in methods for diagnosing a varicella zoster virus infection.

BACKGROUND OF THE INVENTION

In accordance with the classification of the International Committee on Taxonomy of Viruses (ICTV), Van Zoute Vin (VZV) is assigned to the Herpesviridae family. In 75% of cases, primary infections take place not later than the age of 15 and usually take an asymptomatic course. By contrast, infection of adults who have not previously had any contact with the virus and in persons who are naturally or therapeutically immunosuppressed can be associated with severe symptoms. Infection of the fetus also leads to severe symptoms since the virus is able to cross the placenta, and maternal antibodies afford no protection at this time. Following primary infection, the virus persists throughout life in sensory ganglia. After reactivation, the VZV spreads over the peripheral nerves in sensory ganglia and then gives rise to herpes zoster.

Seventy open reading frames (ORF), including the open reading frames for the known glycoproteins gpI (ORF 68), gpII (ORF 31), gpIII (ORF 37), gpIV (ORF 67), gpV (ORF 14) and gpVI (ORF 60), can be deduced from the sequence of the VZV genome, which has been completely elucidated and has a length of 124,884 bp (Dumas strain; (A. J. Davison & J. E. Scott (1986), J. Gen. Virol. 67, 1759–1816)). In each case, the amino acid sequence deduced from the nucleotide sequence displays differing degrees of homology with glycoproteins gE, gB, gH, gI, gC and gL of herpes simplex virus (HSV). However, there is nothing to suggest that the sequence homology can also imply a homologous function. The open reading frames of glycoproteins gpI, gpII, gpIII and gpV have been confirmed by means of molecular biology.

Unlike the more thoroughly investigated glycoprotein gB of HSV, few data are available with regard to the homologous protein of VZV, i.e. gpII. The corresponding investigations have been confined to the biosynthesis of gpII and the importance of gpII for virus neutralization (P. M. Keller et al. (1986), Virologie 152, 181–191; M. Masser et al. (1993), J. Gen. Virol. 74, 491–494).

Ellis et al. (E.P. 0210931B1) have confirmed understanding of ORF 31, which is assigned to gpII. In addition, Ellis et al. describe the purification of gpII from VZV-infected MRC 5 cells (human fibroblasts) and its use for preparing virus-neutralizing antibodies from guinea pigs. P. M. Keller et al. (1986), Virologie 152, 181–191 and M. Masser et al. (1993), J. Gen. Virol. 74, 491–494 make use of, inter alia, gpII, which was purified from VZV-infected cells by means of affinity chromatography, for determining the VZV-specific antibody titer of human sera. Following deletion of the carboxyterminal region, A. Bollen (E.P. 0405867 A1; U.S. Pat. No. 371,772) expressed gpII, which lacked its membrane anchor, using the baculovius expression system in SF9 cells and, by means of constitutive expression in CHO cells, for preparing a VZV vaccine. Furthermore, E. H. Wasmuth & W. J. Miller ((1990), J. Med. Virol. 32, 189–193) used glycoproteins (including gpII), which have been affinity-purified from VZV-infected cells in a glycoprotein or dot ELISA, for demonstrating sensitivity of these test methods and also that antibody titers produced correlated with protection against VZV infection. However, none of the above-mentioned publications provides information for preparing adequate quantities of glyco-protein gpII to set up a test on a diagnostically relevant scale. Furthermore, no suitable investigation of the detailed structure of gpII or, in particular, immuno-reactive epitopes on the gpII protein have been disclosed.

There are a very wide variety of serological methods for examining the status of VZV immunity. These methods range from radioimmunoassay (RIA), enzyme-linked immunosorbentassay (ELISA), fluorescent antibody membrane antigen assay (FAMA) and immunofluorescence test (IFT) to complement fixation (CF). These methods mainly detect VZV-specific antibodies. Virus material that has been isolated after elaborate culture on human fibroblast cultures and purified for diagnostic use by special methods is frequently employed as the antigen.

Unfortunately, the isolation of VZV antigens from infected fibroblasts is dangerous and carries the danger of infecting laboratory personnel. In addition, the preparation is very costly and time-consuming because, inter alia, the virus is not released from the infected cells and special purification methods are required. In order to use the antigen for an immunochemical test without prior purification, the VZV-infected cells are disrupted by ultrasonication and the antigen is used directly, after dilution, for coating microtitration plates, for example. Use of this method can give rise to false-positive results, and thus incorrect diagnosis. This is because cell-specific antigens (for example, from autoimmune disease), generally also are bound to the solid phase (in this case microtitration plate wells) along with virus-specific antigens. Other test methods based on purified viral glycoproteins, such as glycoprotein ELISA, require purification methods that are markedly more elaborate and involve much greater loss. Thus, it has scarcely been feasible to set up immunochemical diagnostic tests on a relatively large scale. Cross reactivities with HSV-specific antibodies, and false-positive results due to this, are also frequently observed in glycoprotein ELISA, due to marked homology between glycoproteins of the α-herpesviruses.

SUMMARY OF THE INVENTION

In one embodiment of the invention, an immunoreactive peptide is provided that is homologous with the AA 450 to 655 region of VZV gpII. In another embodiment, the peptide essentially comprises the region encompassing AA 450 to 655 of gpII of VZV. In another embodiment, the region corresponds to AA 505 to 647 and in another embodiment, the region corresponds to AA 517 to 597. In another embodiment, the region corresponds to AA 535 to 584 and in another embodiment the region corresponds to AA 545 to 582.

Other embodiments of the invention provide nucleic acid that hybridizes under stringent conditions with the nucleic acid depicted in FIGS. 2A and 2B and which encode a peptide that is recognized by antibodies which are directed against VZV but not by antibodies which are directed against other herpes viruses. In further embodiments, the invention provides an immunochemical method which uses an immunoreactive peptide as claimed herein for detecting antibodies against VZV in a sample and test kits that contain one or more of the peptides or nucleic acids as described herein. Other embodiments of the invention are readily appreciated, as described further in the specification.

BRIEF DESCRIPTION OF THE FIGURES

FIG. 1 depicts amino acid residues 450–655 of gpII of VZV (SEQ ID NO: 2).

FIGS. 2A and 2B show a nucleotide sequence (SEQ ID NO: 1) that corresponds with the amino acid sequence shown in FIG. 1.

FIGS. 3A and 3B show data obtained from an ELISA test in accordance with an embodiment of the invention.

FIGS. 4A and 4B show data obtained from another ELISA test in accordance with an embodiment of the invention.

FIG. 5 is a list of sequences described in the specification.

DETAILED DESCRIPTION OF THE INVENTION

One possible solution to the above mentioned problems lies in using recombinant proteins, which can be prepared in large quantity in a heterologous system, e.g. in *Escherichia coli* (*E. coli*). There is no possibility of infecting personnel with VZV when this system is used. Furthermore, this system provides the possibility of differential diagnosis which is geared to specific virus proteins in particular, the reactive region of the VZV proteins can be delimited to the extent that cross reactivities with antibodies which are specific for other herpes viruses can be virtually or completely ruled out. A protein which meets these conditions can also be expressed as a hybrid protein, with either a host-specific protein, for example the *E. coli* maltose-binding protein (MBP), or a N-terminally located sequence composed of 6 histidine residues (His tag) contributing, as fusion partner, to the stabilization of the expression product. A hybrid protein can then, following a single-step affinity purification, be used directly, in almost pure and consequently contamination-free form, for coating diagnostically utilizable surfaces, for example an ELISA microtitration plate. Proteins which meet the abovementioned criteria have not so far been described for the VZV system.

The inventors surprisingly located diagnostically utilizable epitopes, which lie in the region encompassing amino acid positions 450 to 655, on glycoprotein gpII of VZV.

The present invention consequently relates to an immunoreactive peptide which is homologous with the region encompassing AA 450 to 655 of gpII of VZV or which essentially contains the region encompassing amino acids 450 to 655 of gpII. In this context, preference is given to those peptides in which the region corresponds to amino acids 505 to 647 or to amino acids 517 to 597, particularly preferably to amino acids 535 to 584 or, very particularly preferably, to amino acids 545 to 582.

The present invention consequently relates to an immunoreactive peptide (a peptide that cross-reacts with antibody specific to gpII) that is homologous with the AA 450 to 655 region of VZV gpII or which essentially comprises the amino acids 450 to 655 region of gpII. By "essentially comprises the amino region of gpII" is meant a homologous portion of this region that maintains an epitope of the gpII, as easily determined by cross-reactivity with antibody against gpII, and more specifically may be a smaller portion corresponding to amino acids 505 to 647 or to amino acids 517 to 597, particularly to amino acids 535 to 584 or, very particularly, to amino acids 545 to 582.

Immunoreactive peptides that display naturally varying amino acid sequences due to VZV strain variations are expressly included in this context. The term "homologous" as used here, has the customary meaning known to the skilled artisan. The term is used to mean according to one embodiment of the invention, in reference to a comparison of two peptides or proteins, that when the sequences of the two molecules are aligned side by side, the degree of correspondence (% identical amino acids at the positions) is equal to or less than the variation that is possible within naturally occurring sequences. In one embodiment of the invention this variation is equal or less than 5% In another embodiment this variation is equal to or less than 7%. In yet another embodiment, this variation is equal to or less than 10%. In such embodiments, the sequence can be modified easily and still remain immunoreactive, and thus useful for the invention. Still further, conservative amino acid changes can be made (as known to the skilled artisan) which maintain immunoreactivity.

Those immunoreactive peptides which exhibit naturally varying amino acid sequences owing to VZV strain variations are also expressly intended to be included in this context.

The invention furthermore relates to nucleic acids, i.e. DNA or RNA, which encode the abovementioned immunoreactive peptides according to the invention. This is, in particular, the nucleic acid which has the sequence depicted in FIGS. 2A and 2B. However, in addition to this, nucleic acids which hybridize with the abovementioned nucleic acids under stringent conditions and encode peptides which are recognized by antibodies which are directed against VZV but not by antibodies which are directed against other herpes viruses are also intended to be concomitantly included.

The invention also relates to immunoreactive peptides which can be prepared by expressing the nucleic acid having the sequence depicted in FIGS. 2A and 2B, or one of the abovementioned nucleic acids which hybridizes under stringent conditions, with all the peptides being characterized by the fact the they are recognized by antibodies which are directed against VZV but not by antibodies which are directed against other herpes viruses. The stringency of hybridization used in this embodiment of the invention is determined by a number of factors during hybridization and during the washing procedure including temperature, ionic strength, length of time and concentration of formamide. These factors are outlined in, for example, Sanibrook et al. (Sambrook et al., *Molecular Cloning A Laboratory Manual* $2^{nd}$ *Ed.*, 1989 Cold Spring Harbor Laboratory Press, Cold Spring Harbor, N.Y.), which is incorporated by reference.

The present invention furthermore relates to an immunochemical method, which makes it possible to detect antibodies against VZV. In this method, one or more of the immunoreactive peptides is/are brought into contact with a sample, for example a blood sample, plasma sample or serum sample from a patient, which sample is to be investigated for the presence of VZV-specific antibodies. It is then subsequently determined, using methods with which the skilled person is familiar, whether antibodies from the sample bind to the immunoreactive peptides employed or enter into another immunological interrelationship, for example a competition, with these peptides.

The present invention additionally relates to the use of the abovementioned nucleic acids according to the invention for detecting VZV by means of nucleic acid hybridization.

The present invention furthermore relates to a test kit for detecting antibodies against VZV, which kit comprises an immunoreactive peptide according to the invention, and to a test kit for detecting VZV, which kit comprises a nucleic acid according to the invention.

Expression of glycoprotein II (gpII) in fragmented form in a bacterial system was used to locate diagnostically utilizable immunoreactive regions. It is known that the gpII-specific immune response appears first upon infection with VZV. It is only later that that the immune responses against gpI and gpIII make their appearance. However, information about the bacterial expression of gpII, or about its immunorelevant epitopes, was not previously available.

The entire ORF31 for gpII, as described by Ellis et al. (E.P. 0210931B1), was amplified from genomic VZV DNA (Ellen strain) and cloned into the prokaryotic expression vector pMAL-p2 (NEB), which enables the inserted DNA fragment to be expressed as an MBP hybrid protein. However, the complete ORF31 was found not to be suitable for bacterial expression. For this reason, expression of constituent regions of ORF31 was investigated in the pMAL system. Corresponding expression products were detected in the case of all the fragments (fragment size between 400 and 600 bp). A serum pool, comprising 25 VZV-reactive human sera, was used to examine the reactivity of the expression products. Only one of the fragments was found to be immunoreactive. This was a 206 AA fragment (FIG. 1), which was homologous to AA 450–655 of gpII. In order to further delimit the immunoreactive epitope, constituent regions of this fragment were taken for expression in the pMAL system. With the aid of immunoscreening, it was shown that the fragments which encode AA 505–647 (pMAL-427-gpII), AA 517–597 (pMAL-240-gpII) or AA 535–584 (pMAL-149-gpII) are immunoreactive. It was possible to categorize the region of 206 AA 535–584 as being the main immunoreactive epitope of gpII.

FIG. 1 shows amino acid residues 450–655 of gpII (Ellen strain). A total of 206 AA; theoretical molecular weight 23.5 kDa. The emphasized region corresponds to the immunoreactive domain. The underlined AA is the AA which has been replaced as compared with the Dumas strain. The numbering of the amino acids begins with the methionine (start codon) of the published gpII sequence (A. J. Davison & J. E. Scott (1986), J. Gen. Virol. 67, 1759–1816).

The corresponding nucleotide sequence of the amino acid sequence from FIG. 1, is shown in FIGS. 2A and 2B. In order to evaluate this domain in immunological test methods, the gpII sequence encoding the 206 AA-long region was subcloned into the vector pQE (Qiagen). The vector construct was designated pQE-gpII*. This vector possesses a C-terminally located histidine tag (6×His) as the fusion moiety, so that the immunoreactivity of the human sera to be tested can be attributed solely to the gpII moiety and it is possible to rule out false-positive results in the immunotesting of VZV-reactive sera.

In an ELISA evaluation, the purified protein which is encoded by plasmid pQE-gpII* gave a sensitivity of 71% (n=49) and a specificity of 100% (n=5) when the calculated cutoff of 305 (average value of the negative sera+3 times the standard deviation) was used or, when the freely selected cutoff of 160 was used, a sensitivity of 82% and a specificity of 80% for IgG diagnosis.

In an alternative ELISA evaluation, the purified protein which is encoded by plasmic pQE-gpII* gave a sensitivity of 23% (n=13) and a specificity of 100% (n=41) when a calculated cutoff of 102 (average value of the negative sera +3 times the standard deviation) was used or, when a freely selected cutoff of 70 was used, a sensitivity of 61.5% and a specificity of 80% for IgM diagnosis. Sensitivity and specificity can be optimized at any time using methods which are known to the skilled person.

The present invention is illustrated by the following examples which should not, however, in any way be regarded as limiting the scope of the invention.

EXAMPLES

Example 1

Isolation of Viral VZV Virions and DNA Extraction

Virions were released from VZV-infected fibroblasts by means of ultrasonication. The viruses were purified from cellular constituents by passing through a linear sucrose gradient (20–70% (w/v)) Following incubation with DNase I, viral DNA was released from virions by treating with proteinase K and sodium dodecyl sulfate (SDS). After extraction with phenol/chloroform, viral DNA was precipitated with ethanol.

Example 2

Cloning ORF31 and Subcloning the Immunoreactive Fragment

The viral DNA (see Example 1) was used as the template for amplifying ORF31, which encodes gpII. The following primers were used as amplification oligonucleotides:

gpIIH 5' GGAATTCCTTCTATGTTTGTTACGGCGGTTG 3';

gpIIR 5' GCTCTAGAGCATTTACACCCCCGTTACATTCTCG 3'.

While these oligonucleotides are complementary to the corresponding segment of the published sequence (A. J. Davison & J. E. Scott. (1986), J. Gen. Virol. 67, 1759–1816), they contain, at their 5' termini, a restriction cleavage site sequence which does not hybridize with the template DNA. After amplification had taken place, the amplificate, of 2630 bp in size, was cleaved at the terminus with restriction enzymes EcoRI and XbaI and ligated into the expression vector pMAL-p2 which had previously been linearized with EcoRI and XbaI (pMALp-2-ORF31). The entire ORF31 was sequenced in an overlapping, bidirectional manner. It possessed a base substitution of cytosine by thymidine at nucleotide position 1550, which led to the placement of serine by phenylalanine at the amino acid level.

In order to subclone the immunoreactive region, the inserted region was excised from vector pMAL-p2-ORF31 using the above-mentioned restriction enzymes, gel-purified and then digested with ApoI. The resulting 610 bp ApoI fragment was likewise gel-purified and subcloned into the EcoRI cleavage site of vector pMAL-c2. The vector was designated pMAL-gpII*. After the immunoreactivity had been confirmed, the coding region was subcloned into vector pQE. For this, the 610 bp fragment was excised from vector pMAL-gpII* with the restriction enzymes XmnI and HindIII and subcloned into the SmaI/HindIII restriction cleavage sites of vector pQE32. The vector was designated pQE-gpII*.

Example 3

Subcloning the Immunoreactive Epitope

By carrying out amplifications using vector pMAL-gpII* as the template DNA and the oligonucleotides:

5'CGGGATCCCGTGTTAAAGCTCGTATTCTCGGCGACG3' and

5'CCCAAGCTTTAATCCTGTATCCCGCAGCTCGTCTCT3';

5'CGGGATCCGTTTCTAATTGTCCAGAACTGGGATCAG3' and

5'CCCAAGCTTATACGTAGTGATGCCCAAATAGAAAA3' or

5'CGGGATCCTCTATGAGGGTATCTGGTAGTACTACGCGTT3' and

5'CCCAAGCTTAGCCACGCATGGTTCTAACAGATC3' it was possible to obtain a 427 bp fragment, a 240 bp fragment or a 149 bp fragment, each of which was subcloned, after having been subjected to restriction digestion with the enzymes BamHI and HindIII, into vector pMAL-c2 which had been linearized with BamHI and HindIII. The resulting constructs were designated pMAL-427-gpII, pMAL-240-gpII and pMAL-149-gpII, respectively.

Example 4 a) Preparation of the Recombinant Protein pQE gpII*

The recombinant protein pQE gpII was expressed and purified by metal affinity chromatography under denaturing conditions in accordance with the manufacturer's instructions (from Clontech, Talon Metal Affinity Resin, PT1320-1).

b) Preparation of Solid Phase I (System According to the Invention)

Type B microtitration plates (from Greiner) were incubated, at 4° C. for 18 hours, with 110 µl per well of coating solution (4 µg of recombinant pQE gpII/ml in 50 mM sodium carbonate buffer, pH 9.5). The wells of the microtitration plates were then washed three times with in each case 300 µl of wash solution (50 mMTris/EDTA, pH 7.0–7.4+0.5% BSA).

c) Enzyme Immunoassay for Detecting VZV IgG Antibodies

In order to detect anti-VZV IgG in the enzyme immunoassay, 100 µl of the sera which had been prediluted 1:100 in POD sample buffer (Behring Diagnostics GmbH, OWBE 945) were in each case pipetted into the microtitration plate which had been prepared as described in Example 4b, and the plate was incubated at 37° C. for 1 h.

After the plate had been washed 3 times with POD wash solution (Behring Diagnostics GmbH, OSEW 965), 100 µl of the anti-human IgG/POD conjugate (Behring diagnostics GmbH Ch. 243713), diluted 1:50 in Microbiol conjugate buffer (Behring Diagnostics GmbH, OUWW 935), were pipetted in. The 1-hour incubation (at 37° C.) was terminated with three further washing steps. The bound peroxidase activity, which correlates directly with the number of bound VZV antibody molecules, was determined by adding $H_2O_2$/tetramethylbenzidine (Behring Diagnostics GmbH, OUVG 945). After 30 minutes at room temperature, substrate conversion was stopped by adding 0.5 M sulfuric acid (Behring Diagnostics GmbH, OSFA 965) and the extinction coefficient was measured at 450 nm.

Anti-VZV antibody-positive and anti-VZV antibody-negative sera were investigated both in the Enzygnost anti-VZV/IgG reference system (Behring Diagnostics GmbH, OWLT 155) and in the enzyme immunoassay according to the invention. The results (extinction units) of the investigation are shown in FIGS. 3A and 3D. When evaluated in the ELISA, the purified pQE-gpII* protein gave a sensitivity of 69% (n=52) and a specificity of 94% (n=16) using the calculated cutoff of 331 (average value of the negative sera+3 times the standard deviation) or, when the freely selected cutoff of 335 was used, a sensitivity of 69% (n=52) and a specificity of 100% (n=16) for the IgG diagnosis.

Example 5

Enzyme Immunoassay for Detecting VZV IgM Antibodies

The enzyme immunoassay for detecting anti-VZV IgM was carried out as follows: the sera were diluted beforehand 1:50 in POD sample buffer (Behring Diagnostics GmbH, OWBE 945) and then preincubated at room temperature for 15 minutes with RF adsorbent (Behring Diagnostics GmbH, OUCG 945) in the ratio of 1:2. 100 µl of the sera, which had been prediluted as described above, were in each case incubated, at 37° C. for 1 h, in the wells of the microtitration plates which had been prepared as described in Example 4b.

After the plates have been washed three times with POD wash solution (Behring Diagnostics GmbH, OSEW 965), 100 µl of anti-human IgM/POD conjugate (Behring Diagnostics GmbH Ch. 4241313), diluted 1:25 in Microbiol conjugate buffer (Behring Diagnostics GmbH, OUWW 935), were pipetted in The 1-hour incubation (at +37° C.) was terminated by three further washing steps. The bound peroxidase activity, which correlates directly with the number of bound VZV antibody molecules, was determined by adding $H_2O_2$/tetramethylbenzidine (Behring Diagnostics GmbH, OUVG 945). After 30 minutes at room temperature, substrate conversion was stopped by adding 0.5 M sulfuric acid (Behring Diagnostics GmbH, OSFA 965) and the extinction at 450 nm was measured.

Figure 4B:
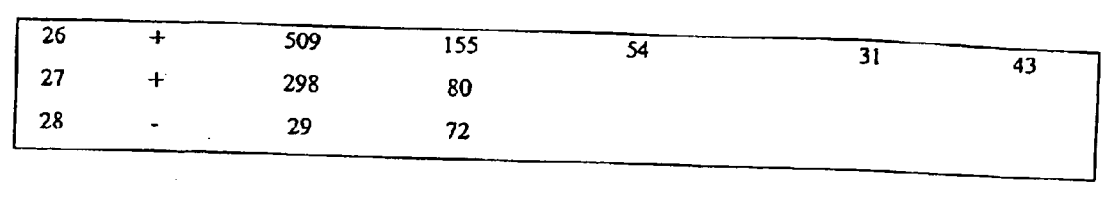

Anti-VZV-positive and anti-VZV-negative sera were investigated both in the Enzygnost anti-VZV/IgM reference system (Behring Diagnostics GmbH, OWLW 155) and in the enzyme immunoassay according to the invention. The results (extinction units) of the investigation are shown in FIGS. 4A and 4B. When evaluated in the ELISA, the purified pQE-gpII* protein gave a sensitivity of 38% (n=13) and a specificity of 100% (n=41) when a calculated cutoff of 102 (average value of the negative sera+3 times the standard deviation) was used or, when a freely selected cutoff of 96 was used, a sensitivity of 38% (n=13) and a specificity of 100% (n=41) for the IgM diagnosis.

Each reference cited herein is hereby incorporated in its entirety by reference. The priority application 19757769.9 filed Dec. 23, 1997 is herein incorporated in its entirety by reference.

SEQUENCE LISTING

<160> NUMBER OF SEQ ID NOS: 10

<210> SEQ ID NO 1
<211> LENGTH: 618
<212> TYPE: DNA
<213> ORGANISM: Varicella Zoster Virus
<220> FEATURE:
<221> NAME/KEY: CDS
<222> LOCATION: (1)..(618)

<400> SEQUENCE: 1

```
gaa ttt gct atg ctc cag ttt aca tat gac cac att caa gag cat gtt        48
Glu Phe Ala Met Leu Gln Phe Thr Tyr Asp His Ile Gln Glu His Val
 1               5                  10                  15 aat gaa atg ttg gca cgt atc tcc tcg tcg tgg tgc cag cta caa aat        96
Asn Glu Met Leu Ala Arg Ile Ser Ser Ser Trp Cys Gln Leu Gln Asn
            20                  25                  30 cgc gaa cgc gcc ctt tgg agc gga cta ttt cca att aac cca agt gct       144
Arg Glu Arg Ala Leu Trp Ser Gly Leu Phe Pro Ile Asn Pro Ser Ala
        35                  40                  45 tta gcg agc acc att ttg gat caa cgt gtt aaa gct cgt att ctc ggc       192
Leu Ala Ser Thr Ile Leu Asp Gln Arg Val Lys Ala Arg Ile Leu Gly
 50                  55                  60 gac gtt atc ttc gtt tct aat tgt cca gaa ctg gga tca gat aca cgc       240
Asp Val Ile Phe Val Ser Asn Cys Pro Glu Leu Gly Ser Asp Thr Arg
 65                  70                  75                  80 att ata ctt caa aac tct atg agg gta tct ggt agt act acg cgt tgt       288
Ile Ile Leu Gln Asn Ser Met Arg Val Ser Gly Ser Thr Thr Arg Cys
                 85                  90                  95 tat agc cgt cct tta att tca ata gtt agt tta aat ggg tcc ggg acg       336
Tyr Ser Arg Pro Leu Ile Ser Ile Val Ser Leu Asn Gly Ser Gly Thr
            100                 105                 110 gtg gag ggc cag ctt gga aca gat aac gag tta att atg tcc aga gat       384
Val Glu Gly Gln Leu Gly Thr Asp Asn Glu Leu Ile Met Ser Arg Asp
        115                 120                 125 ctg tta gaa cca tgc gtg gct aat cac aag cga tat ttt cta ttt ggg       432
Leu Leu Glu Pro Cys Val Ala Asn His Lys Arg Tyr Phe Leu Phe Gly
130                 135                 140 cat cac tac gta tat tat gag gat tat cgt tac gtc cgt gaa atc gca       480
His His Tyr Val Tyr Tyr Glu Asp Tyr Arg Tyr Val Arg Glu Ile Ala
145                 150                 155                 160 gtc cat gat gtg gga atg att agc act tac gta gat tta aac tta aca       528
Val His Asp Val Gly Met Ile Ser Thr Tyr Val Asp Leu Asn Leu Thr
                165                 170                 175 ctt ctt aaa gat aga gag ttt atg ccg ctg caa gta tat aca aga gac       576
Leu Leu Lys Asp Arg Glu Phe Met Pro Leu Gln Val Tyr Thr Arg Asp
            180                 185                 190 gag ctg cgg gat aca gga tta cta gac tac agt gaa att caa                618
Glu Leu Arg Asp Thr Gly Leu Leu Asp Tyr Ser Glu Ile Gln
        195                 200                 205
```

<210> SEQ ID NO 2
<211> LENGTH: 206
<212> TYPE: PRT
<213> ORGANISM: Varicella Zoster Virus

<400> SEQUENCE: 2

```
Glu Phe Ala Met Leu Gln Phe Thr Tyr Asp His Ile Gln Glu His Val
 1               5                  10                  15

Asn Glu Met Leu Ala Arg Ile Ser Ser Ser Trp Cys Gln Leu Gln Asn
```

```
                    20                  25                  30
Arg Glu Arg Ala Leu Trp Ser Gly Leu Phe Pro Ile Asn Pro Ser Ala
        35                  40                  45

Leu Ala Ser Thr Ile Leu Asp Gln Arg Val Lys Ala Arg Ile Leu Gly
    50                  55                  60

Asp Val Ile Phe Val Ser Asn Cys Pro Glu Leu Gly Ser Asp Thr Arg
65                  70                  75                  80

Ile Ile Leu Gln Asn Ser Met Arg Val Ser Gly Ser Thr Thr Arg Cys
                85                  90                  95

Tyr Ser Arg Pro Leu Ile Ser Ile Val Ser Leu Asn Gly Ser Gly Thr
            100                 105                 110

Val Glu Gly Gln Leu Gly Thr Asp Asn Glu Leu Ile Met Ser Arg Asp
        115                 120                 125

Leu Leu Glu Pro Cys Val Ala Asn His Lys Arg Tyr Phe Leu Phe Gly
    130                 135                 140

His His Tyr Val Tyr Tyr Glu Asp Tyr Arg Tyr Val Arg Glu Ile Ala
145                 150                 155                 160

Val His Asp Val Gly Met Ile Ser Thr Tyr Val Asp Leu Asn Leu Thr
                165                 170                 175

Leu Leu Lys Asp Arg Glu Phe Met Pro Leu Gln Val Tyr Thr Arg Asp
            180                 185                 190

Glu Leu Arg Asp Thr Gly Leu Leu Asp Tyr Ser Glu Ile Gln
        195                 200                 205

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
ggaattcctt ctatgtttgt tacggcggtt g                              31

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 4
gctctagagc atttacaccc ccgttacatt ctcg                           34

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 5
cgggatcccg tgttaaagct cgtattctcg gcgacg                         36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 6
cccaagcttt aatcctgtat cccgcagctc gtctct                                 36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 7
cgggatccgt ttctaattgt ccagaactgg gatcag                                 36

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
cccaagctta tacgtagtga tgcccaaata gaaaa                                  35

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 9
cgggatcctc tatgagggta tctggtagta ctacgcgtt                              39

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 10
cccaagctta gccacgcatg gttctaacag atc                                    33
```

We claim:

1. A method for detecting antibodies against varicella zoster virus (VZV) in a sample suspected of containing antibodies to VZV, comprising the step of contacting an immunoreactive polypeptide of SEQ ID NO: 2 with the sample, wherein the immunoreactive polypeptide has an amino acid sequence that comprises the region encompassing AA450 to AA655 of gpII of VZV, and detecting bound antibody, wherein detected bound antibody indicates the presence of antibody in the sample.

2. A method for detecting antibodies against VZV in a sample suspected of containing antibodies to VZV, comprising the step of contacting an immunoreactive polypeptide of SEQ ID NO: 2 with the sample, wherein the immunoreactive polypeptide is encoded by a nucleic acid sequence of 618 bp or less that hybridizes under stringent conditions to a nucleic acid of SEQ ID NO: 1 and the polypeptide is recognized by antibodies that bind SEQ ID NO: 2; and detecting bound antibody, wherein the detection of bound antibody indicates the presence of antibody In the sample.

3. A method for detecting antibodies against Varicella Zoster virus (VZV) in a sample suspected of containing antibodies to VZV, comprising the steps of:

a) contacting an immunoreactive polypeptide comprising an amino acid sequence of SEQ ID NO: 2, wherein the polypeptide comprises a diagnostically utilizable epitope from the region encompassing amino acid positions 450 to 655 of glycoprotein gpII of VZV; and b) detecting bound antibody, wherein the detection of bound antibody indicates the presence of antibody in the sample.

4. The method of claim 3, wherein the immunoreactive polypeptide comprises a sequence selected from the group consisting of: AA 545 to 582 of glycoprotein gpII of varicella zoster virus (VZV), which correspond to AA 95 to 132 of SEQ ID NO:2; AA 535 to 584 of glycoprotein gpII of VZV, which correspond to AA 85 to 134 of SEQ ID NO:2; AA 517 to 597 of glycoprotein gpII of VZV, which correspond to AA 67 to 147 of SEQ ID NO:2; AA 505 to 647 of glycoprotein gpII of VZV, which correspond to AA 55 to 197 of SEQ ID NO:2; and an amino acid sequence that corresponds to the nucleotide sequence of SEQ ID NO: 1.

5. The method of claim 3, wherein the sample is a blood sample, plasma sample or serum sample.

* * * * *